United States Patent [19]

Ohtani et al.

[11] Patent Number: 5,124,462

[45] Date of Patent: Jun. 23, 1992

[54] PREPARATION OF NORBORNYL SULFONAMIDE DERIVATIVES

[75] Inventors: Mitsuaki Ohtani, Nara; Takaharu Matsuura, Nishinomiya; Yoshinori Hamada, Kawanishi; Shoji Shinomoto, Matsubara, all of Japan

[73] Assignee: Shiongi & Co., Ltd., Osaka, Japan

[21] Appl. No.: 690,295

[22] PCT Filed: Oct. 16, 1990

[86] PCT No.: PCT/JP90/01330

§ 371 Date: Jun. 18, 1991

§ 102(e) Date: Jun. 18, 1991

[87] PCT Pub. No.: WO91/05765

PCT Pub. Date: May 2, 1991

[30] Foreign Application Priority Data

Oct. 18, 1989 [JP] Japan .................................. 1-274428

[51] Int. Cl.$^5$ .................. C07C 311/20; C07D 493/08
[52] U.S. Cl. ...................................... 549/463; 560/12; 562/427; 564/89; 564/93
[58] Field of Search .......................... 549/463; 560/12; 562/427; 564/89, 93

[56] References Cited

U.S. PATENT DOCUMENTS 5,002,972 3/1991 Narisada et al. .................... 514/604

FOREIGN PATENT DOCUMENTS 3720760 1/1989 Fed. Rep. of Germany .
63-139161 6/1988 Japan .

Primary Examiner—Richard L. Raymond

Attorney, Agent, or Firm—Wenderoth, Lind & Ponack

[57] ABSTRACT

A process for preparing a compound of Formula (I):

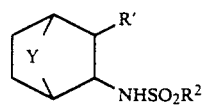

(I)

wherein R' is optionally protected —CH$_2$OH or —COOH; R$^2$ is phenyl or substituted phenyl; and Y is oxygen, methylene, or substituted methylene, which comprises treating a norbornyl acid amide of formula (II):

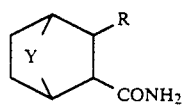

(II)

wherein R is optionally protected —CH$_2$OH or —COOR$^1$; R$^1$ is hydrogen or ester-forming group; and Y is oxygen, methylene, or substituted methylene under the reaction conditions for the Hofmann Rearrangement, and then with a substituted sulfonyl halide of formula (III):

$R^2SO_2X$ (III)

wherein R$^2$ is phenyl or substituted phenyl; and X is halogen atom.

5 Claims, No Drawings

PREPARATION OF NORBORNYL SULFONAMIDE DERIVATIVES

FIELD OF THE INVENTION

This invention relates to a process for preparing norbornyl sulfonamide derivatives useful as intermediates for the preparation of bicycloheptane carboxylic acid derivatives of general formula:

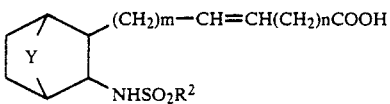

wherein $R^2$ is phenyl or substituted phenyl; Y is oxygen, methylene, or substituted methylene; m is 0 or 1; and n is 3 or 4.

The norbornyl sulfonamide derivative of the invention is shown by formula (I):

wherein R' is optionally protected —$CH_2OH$ or —COOH; $R^2$ is phenyl or substituted phenyl; and Y is oxygen, methylene, or substituted methylene.

Because typical compounds of formula (I) where Y is methylene are known as "norbornane derivatives", the compounds of formula (I) are referred to as "norbornyl sulfonamide derivatives" throughout this specification irrespective of what Y represents.

BACKGROUND OF THE INVENTION

The above-mentioned bicycloheptane carboxylic acid derivatives are clinically important thromboxane $A_2$ ($TXA_2$) receptor antagonists. $TXA_2$ is a member of prostanoids which are synthesized enzymatically from arachidonic acid via prostaglandin $H_2$ ($PGH_2$) as an intermediate, and are known to exhibit many significant biological activities such as aggregation of platelets and contraction of smooth muscles of various organs. Therefore, $TXA_2$ receptor antagonists have been expected to be therapeutically and prophylactically effective on $TXA_2$-associated diseases. Such diseases include myocardial infarction, cerebral infarction, pulmonary embolism, thrombosis, encyopyelitis, renal dysfunction, asthma caused by bronchoconstriction, and the like. It may be also useful to prevent the vascular contraction after a subarchnoidal bleeding, $TXA_2$ shocks after the artery reperfuse of circulation systems or digestive organs, shocks caused by bleeding, septicemia, wound, cardiac dysfunction, endotoxin, acute pancreatitis, burn, or the like. It may be also effective for the prevention of thrombocytopenia during extracorporeal circulation.

In view of the above, the present inventors made extensive studies and found a class of bicyclheptane carboxylic acid derivatives having antagonistic activities against $TXA_2$ [see, Japanese Patent Publication (Kokai) No. 139161/1988]. The carboxylic acids were so far prepared by a process in which a sulfonamide derivative of formula (I) was prepared from 2-alkoxycarbonyl-3-carboxy-norbornane of formula (IV) by means of Curtius Rearrangement according to the following reaction scheme.

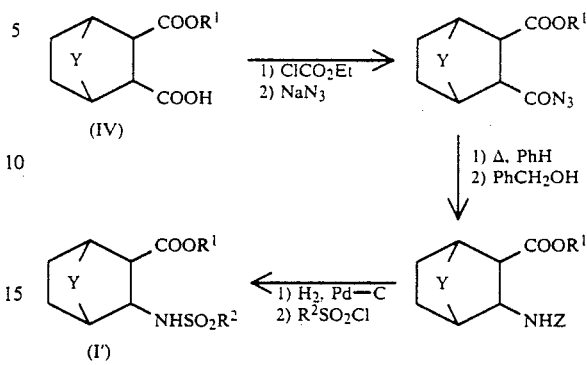

In the reaction scheme, $R^1$ is an ester-forming group; $R^2$ is a phenyl or substituted phenyl; Z is an amino-protecting group; and Y is as defined above. However, the above-mentioned method is not suitable to apply to the total process for the mass-production of the bicycloheptane carboxylic acid derivatives because:

1) it requires a large amount of harmful reagent, $NaN_3$;
2) it generates a poisonous intermediate, an azido compound; and
3) it involves troublesome processes such as protection and deprotection of amino group.

Therefore, it has been highly desired to establish a safe and efficient method for preparing the sulfonamide derivative of formula (I), which in turn makes an advance in the mass-production of the biologically active bicycloheptane carboxylic acid derivatives.

The inventors made extensive investigations with the aim of solving these problems and have now found that the sulfonamide derivative (I) can be obtained efficiently and easily by making a sulfonyl halide react with a norbornyl amine prepared by treating a norbornane derivative having carbamoyl group at the 3-position under the reaction conditions for the "Hofmann Rearrangement" in situ.

DISCLOSURE OF THE INVENTION

Thus, the present invention provides a process for the preparation of a norbornyl sulfonamide derivative of formula (I), which process comprises treating a norbornanoic acid amide of formula (II):

wherein R is optionally protected —$CH_2OH$ or —$COOR^1$; $R^1$ is hydrogen or ester-forming group; and Y is oxygen, methylene, or substituted methylene under the reaction conditions for the Hofmann Rearrangement, and then with a substituted sulfonyl halide of formula (III):

$$R^2SO_2X \qquad (III)$$

wherein $R^2$ is phenyl or substituted phenyl; and X is halogen atom, successively.

The reaction conditions for the Hofmann Rearrangement is well known to those skilled in the art. Generally, it is conducted by treating an acid amide with a bromine or chlorine in the presence of a base followed by hydrolysis of the product. Alternatively, it can be conducted using an alkali solution of an alkali metal hypochlorite such as sodium or potassium hypochlorite or an alkali metal hypobromite such as sodium or potassium hypobromite.

Examples of bases employable for the present process are alkali metal hydroxides such as sodium hydroxide or potassium hydroxide. An alkali solution of sodium hypochlorite or sodium hypobromite can be prepared using a solution of sodium or potassium hydroxide.

After the Hofmann Rearrangement complete, the product is made to react with a substituted sulfonyl halide of formula (III) under a basic conditions to give a desired sulfonamide derivative of formula (I) in the same reaction system. Preferable bases are alkali metal hydroxides such as sodium hydroxide, potassium hydroxide, and the like.

In the preferable embodiment of the present invention, the Hofmann Rearrangement is carried out under the following reaction conditions. Thus, the 3-carbamoylnorbornane of formula (II) is treated with sodium hypochlorite in aqueous sodium hydroxide solution at a temperature in the range of from 0° to 40° C. for 5 minutes to 2 hours and then from 60° to 200° C. for 5 minutes to 4 hours, preferably from 10° to 40° C. for 10 minutes to 2 hours and then 80° to 200° C. for 5 minutes to 2 hours, most preferably from 10° to 40° C. for 10 minutes to 1 hour and then from 80° to 160° C. for 5 minutes to 2 hours.

After the completion of the reaction, a substituted sulfonyl halide and a base such as sodium or potassium hydroxide are added to the reaction mixture to produce the desired sulfonamide derivative of formula (I). The final product (I) can be separated and purified from the reaction mixture using a method well-known to one of skill in the art. Typically, the reaction mixture is acidified with hydrochloric acid, extracted with an appropriate organic solvent, preferably ethyl acetate, and concentrated. The residue is then purified by, for example, recrystallization.

For the purpose of the present invention, as disclosed and claimed herein, the following terms are defined as below.

The term "ester-forming group" generally refers to a group which binds to a carboxyl group through an ester bond. Such ester-forming groups can be selected from carboxy-protecting groups commonly used for the preparation of pharmaceutically active substances. For the purpose of the invention, preferred ester-forming groups include optionally substituted hydrocarbon groups such as haloalkyl groups by lower alkyl, lower alkoxyalkyl, alkyl, and the like; or aralkyl or aralkyl having substituent(s) on its aromatic ring; phenacyl or phenacyl having substituent(s) at the phenyl group, and the like.

The term "lower alkyl" refers to a straight or branched saturated hydrocarbon radical having one to eight carbon atoms, including methyl, ethyl, n-propyl, isopropyl, butyl, isobutyl, sec-butyl, tert-butyl, pentyl, isopentyl, neopentyl, 1,2-dimetylbutyl, hexyl, heptyl, octyl, and the like.

The term "lower alkoxy" refers to $C_1$–$C_8$ alkoxy, including methoxy, ethoxy, propoxy, isopropoxy, butoxy, pentoxy, hexyloxy, heptyloxy, octyloxy, and the like.

The term "lower alkoxyalkyl" refers to a group which is formed by replacing a hydrogen atom of any of above lower alkyl groups by any of above lower alkoxy groups. Examples of such a lower alkoxyalkyl group include methoxymethyl, ethoxymethyl, and the like.

The term "haloalkyl" refers to a group which is formed by replacing hydrogen atom(s) with one to four halogen atoms. Examples of the haloalkyl include 2,2,2-trichloroethyl, 2-iodoethyl, and the like.

The term "halogen" refers to chlorine, bromine, iodine and the like.

Examples of an aralkyl or aralkyl having substituent(s) on its aromatic ring include benzyl, p-methoxybenzyl, p-nitrobenzyl, and the like.

Examples of phenacyl or phenacyl having substituent(s) at the phenyl group include phenacyl, p-bromophenacyl, p-nitrophenacyl, and the like.

In the definition of "Y", examples of substituents for the "substituted methylene" are lower alkyl such as methyl, ethyl, and the like.

In the definition of "substituted sulfonyl halide", examples of substituents for the "phenyl or substitued phenyl" include halogen, lower alkyl, lower alkoxy, hydroxy and the like. Examples of substituted sulfonyl halides include benzenesulfonyl chloride, benzenesulfonyl bromide, methoxyphenylsulfonyl chloride, hydroxyphenylsulfonyl chloride, tolylsulfonyl chloride, bromobenzenesulfonyl bromide such as 4-bromobenzenesulfonyl bromide, and the like.

Although all compounds of formula (II) are suitable as a starting material for the method of present invention, a certain class of compounds (II) are especially preferred for the purpose of the invention. Preferred acid amides are those of formula (II) wherein R is optionally protected hydroxymethyl, carboxyl, or alkoxycarbonyl and Y is methylene. The protecting group for the hydroxymethyl group can be selected from those commonly used in the production of pharmaceutically active substances and are capable of binding to the hydroxyl group to form a bond stable under basic conditions. Examples of hydroxy-protecting groups are those derived from ethers such as methoxymethyl, methylthiomethyl, 2-methoxyethoxymethyl, tetrahydropyranyl, 1-ethoxyethyl, benzyl, 4-methoxybenzyl, and the like; and those derived from silylethers such as tert-butyldiphenylsilyl, and the like. Particularly preferred acid amides are those compounds of formula (II) wherein R is hyiroxymethyl or carboxyl and Y is methylene.

Preferred substituted sulfonyl halides are benzenesulfonyl chloride, benzenesulfonyl bromide, and bromobenzenesulfonyl bromide. Particularly preferred substituted sulfonyl halides are benzenesulfonyl chloride and 4-bromobenzenesulfonyl bromide.

According to the present invention, the desired sulfonamide derivatives of formula (I) can be obtained efficiently by introducing a substituted-phenylsulfonyl group to the 3-amino group of an norbornyl amine which is previously prepared by subjecting a norbornanoic acid amide (II) having an optionally substituted hyroxymethtyl, carboxyl or alkoxycarbonyl group at the 2-position and a carabamoyl group at the 3-position to the Hofmann Rearrangement. Thus, the present invention, as described above, provides an one-pot synthesis for the sulfonamide derivatives of formula (I).

The present method is generally applicable to a process for producing any compounds of formula (I), and particularly useful for the production of optically active derivatives of formula (I) which have been hardly synthesized in large quantities so far. As can be seen from the structure, there exists several optical isomers of compound (I) shown by the following configurations and enantiomers thereof.

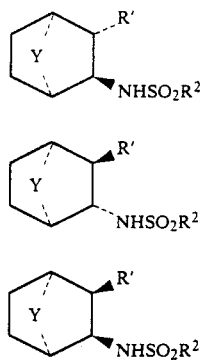

All the above optical isomers are useful intermediate for the synthesis of various organic compounds. Among them, the compound (Ia) is important as an intermediate for the production of a physiologically active optical isomers of 1,4-bridged bicycloheptane carboxylic acid, i.e., (+)-S-145, which is shown by the following structure.

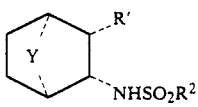

(+)-S-145

The mass-production of said compound (+)-S-145 has been difficult because there were no efficient method for preparing the starting material, compound (Ia). The present invention provides an improved method for preparing the compound (Ia), whereby the mass-production of (+)-S-145 can be facilitated. However, as those skilled in the art will easily appreciate, the present method is not limited to the production of a particular optically-active compound (I) from a given starting material (II), but is generally applicable to the production of any compounds of formula (I) from corresponding starting material (II).

The present invention is herein described mainly concerning to the preparation of the optically active sulfonyl amide derivative of formula (Ia) because it is the starting material in the production for the optically active carboxylic acid (+)-S-145 and analogues thereof. Furthermore, the current process for preparing said compound (Ia) involves aforementioned problems such as poisonous reagents, harmful intermediate, and troublesome processes such as protection or deprotection.

Although the starting material norbornanoic acid amide derivative of formula (II) can be prepared from various substances using any of organic procedures well-known to those skilled in the art, it can be conveniently prepared using above-mentioned 3-carboxylic acid (IV) as a starting material in accordance with the following reaction scheme.

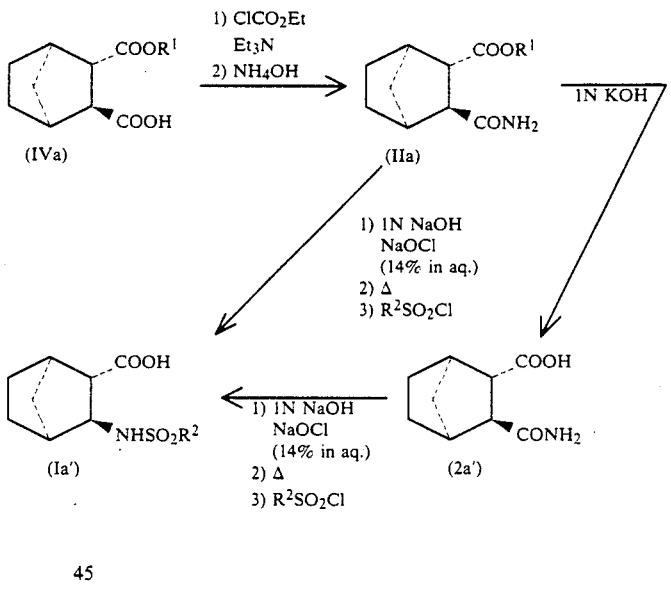

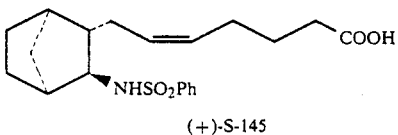

The optically active 3-acid amide (IIa) can be prepared by reacting the optically active 2-alkoxycarbonyl-3-carboxy-norbornane (IVa) with ethyl chloroformate and a tertiary amine such as triethylamine in an organic solvent such as tetrahydrofuran under an atmosphere of nitrogen, and treating the product with ammonia. The resulting 3-acid amide (IIa) is then converted into the 3-amine under the reaction conditions for the Hofmann Rearrangement. Alternatively, the acid amide (IIa) may be hydrolyzed to convert the alkoxycarbonyl group at the 2-position into carboxyl group before the Hofmann Rearrangement.

The hydrolysis can be carried out using a base, for example, potassium hydroxide in an appropriate solvent such as methanol, and the like.

The starting material (IVa) can be conveniently prepared from an aryl acetic monoester such as those described in EP-A-373931 (SHINOGI and Co.) and shown by the following structures:

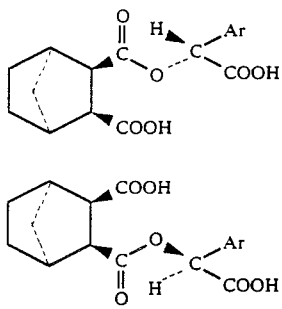

D1

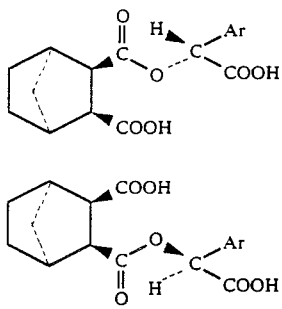

L1 wherein Ar is aryl according to either of following two methods.

(1) Dialkylesterification of a monoester under a neutral to acidic conditions by the use of an acidic catalyst in an alcoholic solvent or methylation reagents such as diazomethane, which is followed by hydrogenolysis to remove the aryl acetic acid moiety.

(2) Heating a monoester in an appropriate alcoholic solvent such as methanol in the presence of a metal salt of said alcohol such as sodium methoxide.

The compound (IVa), an illustrative starting material of the invention, can be conveniently prepared from the above compound $D_1$ according to the method (2). Other optical isomers of compound (IV) are also obtainable in the same manner as above and then converted into corresponding 3-acid amide (II) which gives the desired sulfonamide derivative (I) according to the method of the present invention. The present method is also applicable to other bicyclo [3.1.1.] heptanes such as 2-carbamoyl-3-carboxy-7,7-dimethylbicyclo[3.1.1.] heptane, and the like. The sulfonamide derivative (I) so obtained are useful in the various organic synthetic procedures known to those skilled in the art including those processes described in the Japanese Patent Publication (KOKAI) 139161/1988 to give many pharmaceutically useful substances. For example, the compound (I) is a useful starting material for the preparation of (+)-S-145. A typical process for producing the compound (+)-S-145 comprises the following steps:

a) reducing the sulfonamide (I) with a reducing reagent or catalyst such as lithium aluminum hydride, sodium borohydride, lithium borohydride, lithium trimethoxyaluminum hydride, lithium tri-tert-butoxyaluminum hydride, di-isobutylalminum hydride, diborane, Na-Hg, or the like;

b) oxidating the product as prepared in a) by chromic acid oxidation( PCC or Jones' oxidation), Swern oxidation, or oxidation with pyridine-SO3 complex to obtain 2-aldehyde; and c) reacting the aldehyde prepared in b) with a ylide prepared by treating a methoxymethyl triphenylphosphonium chloride with dimsyl sodium, dimsyl potassium, n-butyl lithium, potassium t-butoxide, sodium amide, sodium hydride, lithium diisopropylamide, and the like under the reaction conditions of the Wittig Reaction for methylene homologation.

The following example is set forth to further describe the invention but in no way meant to be construed as limiting the scope thereof.

Preparation 1

2-Methoxycarbonyl-3-carbamoylnorbornane (2a)

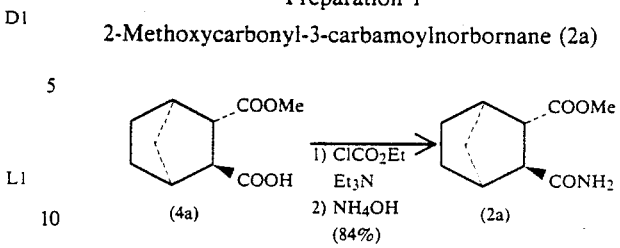

To a solution of 30 g (151 mmol) of 2-Methoxycarbonyl-3-carboxynorbornane (4a) in 300 ml of tetrahydrofuran are added 23.2 ml (151 mmol×1.1) of triethylamine and 15.9 ml (151 mmol×1.1) of ethyl chloroformate at 0° C. in a nitrogen atmosphere and stirred for 25 minutes. After the addition of 30.68 ml (151 mmol×3.0) of 28% aqueous ammonia at the same temperature, the mixture is stirred for 35 minutes and partitioned between ethyl acetate and water. The ethyl acetate layer is separated, washed with 200 ml of 2N HCl and then water, and concentrated under reduced pressure. The residue is recrystallized from ether-petroleum ether to obtain 25.19 g of the titled compound (2a) as colorless prisms. Yield=84.3%; m.p.=110°-112° C.

IR (KBr) cm$^{-1}$: 3435, 3300, 3190, 2960, 1722, 1676, 1658, 1618, 1436, 1415, 1312, 1225, 1201, 1182, 1156, 1115, 671, 608

$[\alpha]_D$ = +42.4°±0.8° (MeOH; c=1.000; 23° C.)

Elemental analysis (as $C_{10}H_{15}O_3N$). Calcd.: C: 60.90; H: 7.67; N: 7.10. Found: C: 60.97; H: 7.68; N: 7.07.

$^1$H NMR(CDCl$_3$—TMS) δ ppm: 1.26–1.70(m,6H), 2.51(b.s,1H), 2.55–2.61(br.m,1H), 2.85(dd,J=5.5,1.5 Hz, 1H), 3.02–3.12(m,1H), 3.68(S,3H), 5.63(br.s,1H)

EXAMPLE 1

2-Carboxy-3-phenylsulfonylaminonorbornane (Ia')

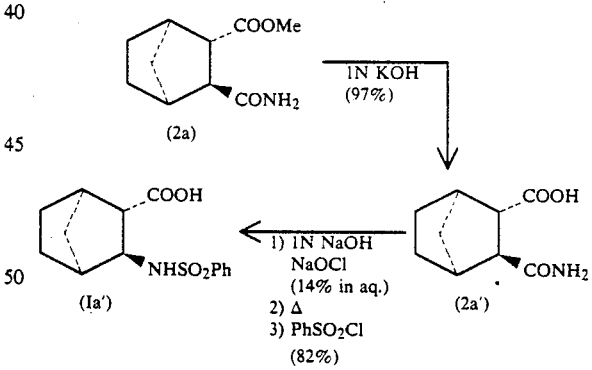

(1) 2-Carboxy-3-carbamoylnorbornane (2a')

To a solution of 104.5 g (0.53 mol) of 3-acid amide prepared in the Preparation 1 in 300 ml of methanol is added 1065 ml (0.53 mol×2.0) of cold 1N KOH at 10°-15° C. and stirred for 3.5 hours at room temperature. The pH of the mixture is adjusted to about 1.0 with conc. HCl under cooling with ice, and the resulting precipitate is collected by filtration and washed with water to obtain the first crop of the titled compound. The filtrate is neutralized to pH 7.0 with 1N NaOH and concentrated under reduced pressure to remove methanol. The residue is partitioned between ethyl acetate and 2N HCl. After salting-out, the aqueous layer is extracted with ethyl acetate. All the ethyl acetate solutions are combined, washed with saline, dried, and concentrated to obtain the second crop of 2-carboxy-3-carbamoylnorbornane (2a') as a crystalline solid. The combined first and second crop of crystals weighed 94 g. Yield=96.9%; m.p.=197°–200° C.

$[\alpha]_D = +42.6° \pm 0.8°$ (MeOH; C=1.014; 24° C.)

IR(KBr) cm$^{-1}$: 3442, 3358, 2960, 3650–2400, 1734, 1722, 1648, 1620, 1393, 1315, 1237, 1190

Elemental analysis (as $C_9H_{13}NO_3$): Calcd.: C: 58.99; H: 7.17; N: 7.65. Found: C: 59.11; H: 7.18; N: 7.79.

$^1$H NMR(CD$_3$OD-TMS) δ ppm: 1.20–1.75(m,6H), 2.56(br.s,1H), 2.78(d,J=5.2 Hz,1H), 3.09(t,J=5.2 Hz,1H), 3.05–3.19(m,1H)

(2) 2-Carboxy-3-phenylsulfonylaminonorbornane (Ia')

To a solution of 141.59 g (275 mmol) of sodium hypochlorite (14.7% aqueous solution) and 206 ml (275 mmol×1.5) of 2N NaOH at 25° C. is added a solution of 50.39 g (275 mmol) of 2-carboxy-3-carbamoylnorbornane (2a'), prepared in above 1, in 138 ml (275 mmol) of 2N NaOH. While the mixture is stirred for 1 hour, the temperature rises upto approximately 30° C. Upon continuous stirring for about 30 minutes on a bath of 125° C., the inner temperature rises upto 100° C. After refluxing for 15 minutes, the reaction mixture is promptly cooled to room temperature and then ice-cooled. The pH of the ice-cooled mixture is adjusted to about 3 to 4 with conc. HCl and washed with ethyl acetate. The aqueous layer is separated, washed with dichloromethane, and adjusted to pH 11 with 5N NaOH. To the resulting mixture is added 52.6 ml (275 mmol×1.5) of benzenesulfonyl chloride at 25° C. and the mixture stirred for 30 minutes with monitoring the pH of the reaction, mixture. When the pH becomes to about 6–7, 55 ml (275 mmol) of 5N NaOH and 17.5 ml (275 mM×0.5) of benzenesulfonyl chloride are added thereto. To the mixture is then added 55 ml (275 mM) of 5N NaOH and stirring is continued for another 40 minutes. Ethyl acetate is added to the reaction mixture and the aqueous layer is separated. The aqueous layer is acidified with conc. HCl and extracted with ethyl acetate. The ethyl acetate layer is dried over MgSO$_4$ and concentrated to obtain a residue. Recrystallization from a mixture of toluene and ethyl acetate gives 66.4 g of 2-carboxy-3-phenylsulfonylaminonorbornane (Ia'). Yield=81.8%; m.p.=157°–159° C.

$[\alpha]_D = -5.3° \pm 0.5°$ (CHCl$_3$; C=1.005; 22.5° C.)
$[\alpha]_{365} = -58.3° \pm 1.0°$ (CHCl$_3$; C=1.005; 22.5° C.)
$[\alpha]_D = +14.7° \pm 0.5°$ (MeOH; C=1.004; 22.5° C.)
$[\alpha]_{365} = +18.2° \pm 0.6°$ (MeOH; C=1.004; 22.5° C.)

IR(KBr) cm$^{-1}$: 3290, 3650–2400, 1705, 1461, 1448, 1424, 1307, 1294, 1260, 1251, 1226, 1155, 1096, 754, 717, 690, 588, 555

Elemental analysis (as $C_{14}H_{17}NO_4S$): Calcd.: C: 56.93; H: 4.80; N: 4.74; S: 10.85. Found: C: 56.75; H: 5.73; N: 4.73; S: 10.81.

$^1$H NMR(CDCl$_3$—TMS) δ ppm: 1.18–1.77(m,6H), 2.08(dd,J=4.8,1.6 Hz,1H), 2.28(br.s, 1H), 2.40–2.50(br.m,1H), 3.77–3.93(m,1H), 5.24(d,J=7.0 Hz,1H), 7.45–7.67(m,3H), 7.81–7.95(m,2H)

EXAMPLE 2

2-Hydroxymethyl-3-phenylsulfonylaminonorbornane (Ia'')

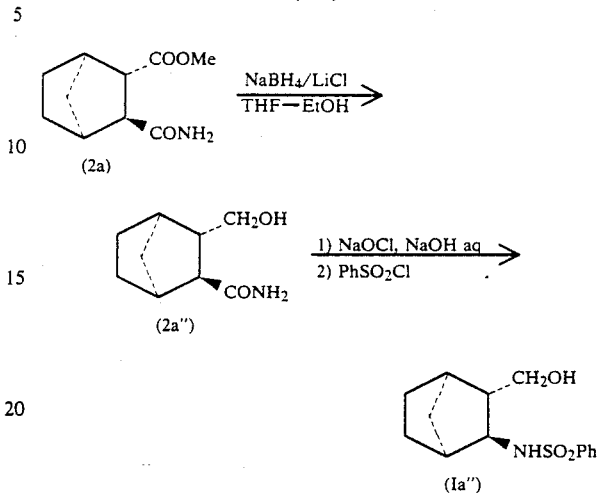

(1) 2-Hydroxymethyl-3-carbamoylnorbornane (2a'')

To a solution of 5.50 g (27.9 mmol) of 2-methoxycarbonyl-3-carbamoylnorbornane (2a) prepared in the Preparation 1 in 57.5 ml of THF are added 3.55 g (83.8 mmol) of lithium chloride, 3.18 g (84.1 mmol) of sodium borohydride, and 115 ml of ethanol and the mixture is stirred at room temperature overnight. A precipitate formed by the addition of sodium chloride-saturated 2N HCl and methyl ethyl ketone is removed by filtration. The organic layer is separated, washed with a saturated brine, dried, and concentrated. The residue is purified by a silica gel column chromatography eluting with chloroform-methanol to give 3.60 g (21.3 mmol) of the titled compound (2a''). Yield=76%; m.p.=135.5°–137.5° C.

Elemental analysis (as $C_9H_{15}NO_2$): Calcd.: C: 63.88; H: 8.93; N: 8.28. Found: C: 63.70; H: 8.86; N: 8.27.

$[\alpha]_D = +55.8° \pm 1.0°$ (MeOH; C=1.004; 25.5° C.)

IR(KBr) cm$^{-1}$: 3760–3010, 2962, 2875, 1660, 1613, 1432, 1048

$^1$H NMR(CD$_3$OD—TMS) δ ppm: 1.15–1.36(m,2H), 1.36–1.70(m,4H), 1.90–2.07(br.m,1H), 2.10–2.20(br.m,1H), 2.20–2.31(m,1H), 2.49(br.s,1H), 3.19–3.48(m,2H)

(2) 2-Hydroxymethyl-3-phenylsulfonylaminonorbornane (Ia'')

To a mixture of 3.09 g (6.02 mmol) of sodium hypochlorite (14.5% aqueous solution) and 4.5 ml (9.00 mmol) of 2N NaOH is added a solution of 1.02 g (6.00 mmol) of the compound (2a'') in 13 ml of water. The mixture is stirred for 20 minutes at room temperature, and then refluxed for 15 minutes. After cooling, 30 ml (15.0 mmol) of 5N NaOH and 1.15 ml (9.00 mmol) of benzenesulfonyl chloride are added thereto at 0° C. and the mixture is stirred at room temperature. When benzenesulfonyl chloride can not be detected on TLC, 0.38 ml (2.98 mmol) of the same compound is added. Three hours later, 2N HCl is added to the reaction mixture. The mixture is extracted with ethyl acetate and the organic layer is separated, washed with water and then saturated brine, dried, and concentrated. The residue is recrystallized from toluene-ethyl acetate to give 1.11 g (3.95 mmol) of 2-hydroxymethyl-3-phenylsulfonylaminonorbornane (Ia").

Yield=65.8%; m.p.=118.5°–120.0° C.

$[\alpha]_D = +8.0 \pm 0.5°$ (CHCl$_3$; C=1.011; 24.0° C.)

Elemental analysis (as C$_{14}$H$_{19}$NO$_3$S): Calcd.: C: 59.75; H: 6.82; N: 4.98; S: 11.39. Found: C: 59.83; H: 6.91; N: 5.02; S: 11.33.

IR(KBr) cm$^{-1}$: 3490, 3130, 2960, 2880, 1479, 1446, 1320, 1162, 1098, 1032, 755, 688, 590, 555

$^1$H NMR (CDCl$_3$—TMS) δ ppm: 1.12–1.68(m,7H), 1.78(br.s,1H), 2.05(d,J=2.8 Hz,1H), 2.10(br.s,1H), 3.05–3.18(m,1H), 3.34(d ABq,A-part,J=7.3,10.8 Hz,1H), 3.42(d ABq,B-part,J=7.6,10.8 Hz,1H), 5.11(d,J=10.0 Hz,1H), 7.45–7.55(m,3H), 7.86–7.96(m,2H)

The following experiments are provided for the purpose of demonstrating the preparation of the 2-formyl compound (d) using, as the starting material, 2-carboxy-3-phenylsulfonylaminonorbornane (Ia') prepared in the above Example 1.

EXPERIMENT 1

$^1$H NMR (CDCl$_3$—TMS) δ ppm: 1.12–1.68(m,7H), 1.78(br.s,1H), 2.05(d,J=2.8 Hz,1H), 2.10(br.s,1H), 3.05–3.18(m,1H), 3.34(dABq,Apart,J=7.3,10.8 Hz,1H), 3.42(dABq,Bpart,J=7.6,10.8 Hz,1H), 5.11(d,J=10.0 Hz,1H), 7.45–7.55(m,3H), 7.86–7.96(m,2H)

(2) PCC Oxidation Step

To a solution of 8.01 g (28.5 mmol) of compound (a) prepared in the above 1) in 600 ml of dichloromethane under a nitrogen atmosphere are added 18.4 g (85.4 mmol) of PCC and 25.1 g of molecular sieves (powder: 4A) and stirred at 30° C. The completion of reaction is confirmed by TLC monitoring about 1 hour later. The mixture is treated by silica gel column chromatography to remove inorganic substances. Fractions eluted with n-hexane-ethyl acetate (2:1) are concentrated to obtain 7.2 g (yield=90%) of aldehyde (b). Being unstable, the aldehyde (b) is used for the next step immediately.

$^1$H NMR (CDCl$_3$—TMS) δ ppm: 1.12–1.84(m,6H), 2.16–2.34(m,2H), 2.40–2.51(br.m,1H), 3.78–3.95(m,1H), 4.90–5.10(br.m,1H), 7.45–7.70(m,3H), 7.82–7.97(m,2H), 9.57(s,1H)

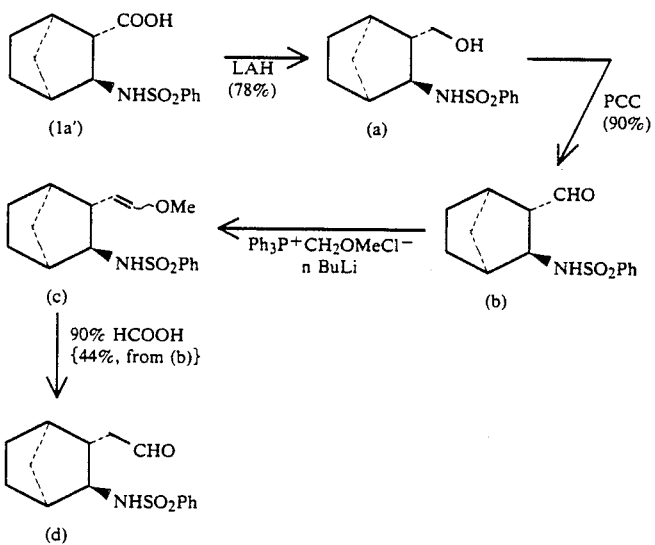

(1) LAH step

To a suspension of 14.8 g (390 mmol) of lithium aluminum hydride in 150 ml of tetrahydrofuran is added dropwise a solution of 28.36 g (96 mmol) of compound (Ia) in 30 ml of tetrahydrofuran over 45 minutes at room temperature. The mixture is stirred for another 1.5 hours at room temperature and ethyl acetate is gradually added to decompose unreacted reagents. Precipitates formed by the addition of water are washed with ethyl acetate by decantation thoroughly. Ethyl acetate extracts are combined, dried over MgSO$_4$, and concentrated under reduced pressure. Recrystallization from toluene-ethyl acetate gives 21.0 g of the titled compound (a) as a colorless prism. Yield=77.8%; m.p.=121°–122° C.

$[\alpha]_D = +7.8° \pm 0.5°$ (CHCl$_3$; C=1.014; 25° C.)

Elemental analysis (as C$_{14}$H$_{19}$NO$_3$S): Calcd.: C: 59.75; H: 6.82; N: 4.98; S: 11.39. Found: C: 59.83; H: 6.91; N: 5.02; S: 11.33.

IR(KBr) cm$^{-1}$: 3495, 3125, 2960, 1479, 1446, 1322, 1182, 1169, 1163, 1096, 1034, 755, 688, 593, 556

(3) Wittic Reaction with n-BuLi

To a suspension of 31.2 g (91mmol) of methoxymethyltriphenylphosphonium chloride in 160 ml of tetrahydrofuran under nitrogen is added 56.0 ml (84 mmol) of n-BuLi (1.6M solution in hexane) at −78° C. After stirring at 0° C. for 25 minutes, the mixture is cooled to −78° C. and a solution of 7.2 g (25.8 mmol) of compound (b) prepared in above 2) in 80 ml of tetrahydrofuran is added thereto. The mixture is warmed up to room temperature over about 35 minutes. After the addition of ice-water, the mixture is extracted with ethyl acetate. The extract is washed with water and concentrated. The residue is treated by a silica gel column chromatography to give the compound (c), which is then dissolved into 5.0 ml of 90% formic acid without purification. After stirring for 1 hour at room temperature, the mixture is neutralized with sodium hydrogencarbonate and extracted with ethyl acetate. The extract is washed with water and concentrated. The residue is purified by silica gel column chromatography to obtain 3.30 g (44% yield) of aldehyde (d). M.p.=100°–103° C.

$^1$H NMR (CDCl$_3$—TMS) δ ppm: 1.15–1.80(m,7H), 1.85(br.s,1H), 2.26–2.56(m,3H), 2.74–2.83(m,1H), 5.21(d,J=8.0 Hz,1H), 7.44–7.63(m,3H), 7.75–7.98(m,2H), 9.57(s,1H)

$[α]_D = +36.5° ± 0.8°$ (CHCl$_3$; C=0.994; 25.5° C.)

Elemental analysis (as C$_{15}$H$_{19}$NO$_3$S): Calcd.: C: 61.40; H: 6.54; N: 4.77; S: 10.93. Found: C: 61.39; H: 6.51; N: 4.90; S: 11.02.

What we claim is:

1. A process for preparing a norbornyl sulfonamide derivative of formula (I):

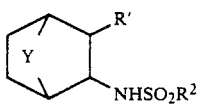 (I)

wherein R′ is optionally protected —CH$_2$OH or —COOH; R$^2$ is phenyl or substituted phenyl; and Y is oxygen, methylene, or substituted methylene, which comprises treating a norbornanoic acid amide of formula (II):

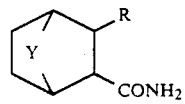 (II)

wherein R is optionally protected —CH$_2$OH or —COOR$^1$; R$^1$ is hydrogen or ester-forming group; and Y is oxygen, methylene, or substituted methylene under the reaction conditions for the Nofmann Rearrangement, and then with a substituted sulfonyl halide of formula (III):

R$^2$SO$_2$X  (III)

wherein R$^2$ is phenyl or substituted phenyl; and X is halogen atom.

2. The process of claim 1 wherein the Hofmann Rearrangement is carried out by treating the acid amide of formula (II) with an alkali metal hypochlorite or alkali metal hypobromite in the presence of alkali metal hydroxide.

3. The process of claim 2 wherein the alkali metal hydroxide is sodium hydroxide.

4. The process of claim 1 wherein the substituted sulfonyl halide is selected from a group consisting of benzenesulfonyl chloride, benzenesulfonyl bromide, and bromobenzenesulfonyl bromide.

5. The process of claim 4 wherein the substituted sulfonyl halide is benzenesulfonyl chloride or benzenesulfonyl bromide.

* * * * *

UNITED STATES PATENT AND TRADEMARK OFFICE
CERTIFICATE OF CORRECTION

PATENT NO. : 5,124,462

DATED : June 23, 1992

INVENTOR(S) : Mitsuaki OHTANI et al.

It is certified that error appears in the above-identified patent and that said Letters Patent is hereby corrected as shown below:

On the title page, item (21), change "690,295 to read --690,925--.

Column 14, line 10, change "Nofmann" to --Hofmann--.

Signed and Sealed this

Twenty-eighth Day of September, 1993

Attest:

BRUCE LEHMAN

*Attesting Officer*  *Commissioner of Patents and Trademarks*